(12) United States Patent
Lavigne

(10) Patent No.: US 8,277,503 B2
(45) Date of Patent: Oct. 2, 2012

(54) STENT FOR IRRIGATION AND DELIVERY OF MEDICATION

(75) Inventor: Francois Lavigne, Ville Mont-Royal (CA)

(73) Assignee: Intersect ENT, Inc., Palo Alto, CA (US)

( * ) Notice: Subject to any disclaimer, the term of this patent is extended or adjusted under 35 U.S.C. 154(b) by 147 days.

(21) Appl. No.: 12/437,380

(22) Filed: May 7, 2009

(65) Prior Publication Data

US 2009/0275903 A1    Nov. 5, 2009

Related U.S. Application Data

(63) Continuation of application No. 11/511,876, filed on Aug. 29, 2006, now Pat. No. 7,547,323.

(51) Int. Cl.
*A61F 2/18* (2006.01)

(52) U.S. Cl. .......................................... 623/10; 604/514

(58) Field of Classification Search ................... 623/10; 604/514, 28, 93.01, 541; 128/201.18, 207.18
See application file for complete search history.

(56) References Cited

U.S. PATENT DOCUMENTS

| | | |
|---|---|---|
| 858,996 A | 7/1907 | Lamport |
| 2,099,127 A | 11/1937 | Leech |
| 2,431,587 A | 11/1947 | Schnee |
| 2,525,183 A | 10/1950 | Robinson |
| 2,859,518 A | 11/1958 | Cohn |
| 3,363,629 A | 1/1968 | Kuhn |
| 3,469,578 A | 9/1969 | Bierman |
| 3,486,539 A | 12/1969 | Jacuzzi |
| 3,527,220 A | 9/1970 | Summers |

(Continued)

FOREIGN PATENT DOCUMENTS

WO    WO-2004/082525 A2    9/2004

(Continued)

OTHER PUBLICATIONS

Final Office Action mailed on Jul. 17, 2008, for U.S. Appl. No. 11/511,876, filed Aug. 29, 2006, 8 pages.

(Continued)

*Primary Examiner* — Brian Pellegrino
*Assistant Examiner* — Cheryl Miller
(74) *Attorney, Agent, or Firm* — Morrison & Foerster LLP

(57) ABSTRACT

A stent comprises a flexible tube having a proximal end, a distal end, and a passageway extending from said proximal end toward said distal end. A first generally straight tube segment extends from the proximal end while a first generally curved segment extends from an end region of the first generally straight tube segment disposed away from the proximal end of the stent. A second generally straight tube segment extends from an end region of the first curved segment away from the first generally straight tube segment and is arranged at an acute angle relative to the first generally straight tube segment. A second generally curved tube segment extends from one end of the second generally straight tube segment and includes a channel on an exterior surface of the second generally curved tube segment. The first generally curved tube segment and the second generally straight tube segment further include at least one cavity irrigation hole extending from the tube passageway, for providing irrigation fluids into the cavity into which the stent is inserted. At least one segments includes a channel on an exterior surface. The channel is sized to serve as a reservoir to contain a predetermined amount of at least one form of medication for delivery, over a period of time, of the medication to a cavity region proximate which the stent has been inserted.

7 Claims, 4 Drawing Sheets

U.S. PATENT DOCUMENTS

| | | | |
|---|---|---|---|
| 3,540,431 | A | 11/1970 | Mobin-Uddia |
| 3,599,642 | A | 8/1971 | Tindel |
| 3,800,788 | A | 4/1974 | White |
| 3,815,600 | A | 6/1974 | Groves |
| 3,874,388 | A | 4/1975 | King et al. |
| 3,894,539 | A | 7/1975 | Tallent |
| 3,921,636 | A | 11/1975 | Zaffaroni |
| 3,948,254 | A | 4/1976 | Zaffaroni |
| 3,964,488 | A | 6/1976 | Ring et al. |
| 3,993,069 | A | 11/1976 | Buckles et al. |
| 3,993,072 | A | 11/1976 | Zaffaroni |
| 3,993,073 | A | 11/1976 | Zaffaroni |
| 4,007,743 | A | 2/1977 | Blake |
| 4,056,104 | A | 11/1977 | Jaffe |
| 4,102,342 | A | 7/1978 | Akiyama et al. |
| 4,169,292 | A | 10/1979 | Grote |
| 4,207,890 | A | 6/1980 | Mamajek et al. |
| 4,217,898 | A | 8/1980 | Theeuwes |
| 258,531 | A | 3/1981 | Orsing |
| 4,307,723 | A | 12/1981 | Finney |
| 4,389,208 | A | 6/1983 | LeVeen et al. |
| 4,508,535 | A | 4/1985 | Joh et al. |
| 4,627,838 | A | 12/1986 | Cross et al. |
| 4,643,716 | A | 2/1987 | Drach |
| 4,737,141 | A * | 4/1988 | Spits ............... 604/28 |
| 4,755,171 | A | 7/1988 | Tennant |
| 4,863,430 | A | 9/1989 | Klyce et al. |
| 4,964,850 | A | 10/1990 | Bouton et al. |
| 4,981,477 | A | 1/1991 | Schon et al. |
| 5,019,032 | A | 5/1991 | Robertson |
| 5,021,043 | A | 6/1991 | Becker et al. |
| 5,087,244 | A | 2/1992 | Wolinsky et al. |
| 5,139,502 | A | 8/1992 | Berg et al. |
| 5,139,510 | A | 8/1992 | Goldsmith, III et al. |
| 5,169,386 | A | 12/1992 | Becker et al. |
| 5,203,773 | A | 4/1993 | Green |
| 5,245,992 | A | 9/1993 | Nye |
| 5,246,455 | A | 9/1993 | Shikani |
| 5,264,260 | A | 11/1993 | Saab |
| 5,279,610 | A | 1/1994 | Park et al. |
| 5,299,574 | A | 4/1994 | Bower |
| 5,304,123 | A | 4/1994 | Atala et al. |
| 5,342,296 | A | 8/1994 | Persson et al. |
| 5,456,714 | A | 10/1995 | Owen |
| 5,470,320 | A | 11/1995 | Tiefenbrun et al. |
| 5,477,852 | A | 12/1995 | Landis et al. |
| 5,531,721 | A | 7/1996 | Pepin et al. |
| 5,601,594 | A | 2/1997 | Best |
| 5,693,065 | A | 12/1997 | Rains, III |
| 5,709,874 | A | 1/1998 | Hanson et al. |
| 5,897,521 | A * | 4/1999 | Lavigne ............... 604/8 |
| 5,985,307 | A | 11/1999 | Hanson et al. |
| 6,030,402 | A | 2/2000 | Thompson et al. |
| 6,042,561 | A | 3/2000 | Ash et al. |
| 6,149,684 | A | 11/2000 | Herrick |
| 6,171,298 | B1 | 1/2001 | Matsuura et al. |
| 6,183,461 | B1 | 2/2001 | Matsuura et al. |
| 6,491,940 | B1 | 12/2002 | Levin |
| 6,543,452 | B1 | 4/2003 | Lavigne |
| 6,558,368 | B1 | 5/2003 | Voda |
| 6,780,168 | B2 | 8/2004 | Jellie |
| 6,783,522 | B2 | 8/2004 | Fischell |
| D501,677 | S | 2/2005 | Becker |
| 7,073,511 | B2 | 7/2006 | Schroeppel |
| 7,361,168 | B2 | 4/2008 | Makower et al. |
| 7,462,175 | B2 * | 12/2008 | Chang et al. ............... 604/510 |
| 7,547,323 | B2 | 6/2009 | Lavigne |
| 2004/0064083 | A1 | 4/2004 | Becker |
| 2004/0064150 | A1 | 4/2004 | Becker |
| 2004/0116958 | A1 | 6/2004 | Gopferich et al. |
| 2005/0240147 | A1 | 10/2005 | Makower et al. |
| 2005/0245906 | A1 | 11/2005 | Makower et al. |
| 2006/0067982 | A1 | 3/2006 | Haapakumpu et al. |
| 2006/0095066 | A1 | 5/2006 | Chang et al. |
| 2006/0106361 | A1 | 5/2006 | Muni et al. |
| 2006/0190022 | A1 | 8/2006 | Beyar et al. |
| 2007/0005094 | A1 | 1/2007 | Eaton et al. |
| 2007/0073269 | A1 | 3/2007 | Becker |
| 2008/0015540 | A1 | 1/2008 | Muni et al. |
| 2008/0097354 | A1 | 4/2008 | Lavigne |
| 2008/0294255 | A1 * | 11/2008 | Gonzales ............... 623/10 |
| 2009/0062927 | A1 | 3/2009 | Marten et al. |
| 2009/0275882 | A1 | 11/2009 | Lavigne |
| 2009/0306624 | A1 | 12/2009 | Arensdorf et al. |
| 2011/0040320 | A1 | 2/2011 | Keith et al. |
| 2011/0112512 | A1 | 5/2011 | Muni et al. |

FOREIGN PATENT DOCUMENTS

| | | | |
|---|---|---|---|
| WO | WO-2004/082525 | A3 | 9/2004 |
| WO | WO-2005/089670 | A1 | 9/2005 |
| WO | WO-2006/107957 | A2 | 10/2006 |
| WO | WO-2006/107957 | A3 | 10/2006 |
| WO | WO-2008/025156 | A1 | 3/2008 |

OTHER PUBLICATIONS

International Search Report mailed on Dec. 14, 2007, for PCT Patent Application No. PCT/CA2007/001527, filed on Aug. 28, 2007, 1 page.

Non-Final Office Action mailed on Jan. 18, 2008, for U.S. Appl. No. 11/511,876, filed Aug. 29, 2006, 7 pages.

Non-Final Office Action mailed on Mar. 7, 2011, for U.S. Appl. No. 12/437,382, filed May 7, 2009, 6 pages.

Notice of Allowance mailed on Feb. 10, 2009, for U.S. Appl. No. 11/511,876, filed Aug. 29, 2006, 6 pages.

Supplementary European Search Report mailed on Jul. 21, 2009, for European Patent Application No. 07800551.9, filed on Aug. 28, 2007, 6 pages.

Final Office Action mailed on Nov. 18, 2011, for U.S. Appl. No. 12/437,382, filed May 7, 2009, 8 pages.

European Examination Report, mailed on Jan. 26, 2012, for EP Application No. 07800551.9, filed on Aug. 28, 2007, five pages.

European Patent Office Result of Consultation, mailed on Jan. 26, 2012, for EP Application No. 07800551.9, filed on Aug. 28, 2007, four pages.

Non-Final Office Action mailed on Mar. 30, 2012, for U.S. Appl. No. 12/437,382, filed May 7, 2009, six pages.

* cited by examiner

STENT FOR IRRIGATION AND DELIVERY OF MEDICATION

TECHNICAL FIELD

This application is a continuation of U.S. application Ser. No. 11/511,876, filed on Aug. 29, 2006, now U.S. Pat. No. 7,547,323, which is hereby incorporated by reference in its entirety.

TECHNICAL FIELD

The present invention relates to tubes for medical applications and more particularly, to an intubation device for placement through the nasal airway into the sinus cavity or any other irregular cavity having an opening on one side, for treatment, irrigation and dispensing of medicine into the cavity.

BACKGROUND INFORMATION

Intubation devices, in general, are well known in the medical field. Tubes are often inserted into body passageways or cavities of a patient to ventilate, drain, irrigate and/or stent the cavity into which the tube in inserted. Continuing efforts are being made to design intubation devices that are easily and comfortably inserted into a patient, particularly when the tube must be left in place within the patient. It also becomes important to provide for a release of medication in a very controlled way in order to release a measured amount of active medication on long term.

One medical use for an intubation device is in the pre and post operative treatment of chronic rhinosinusitis (CRS). CRS is a disease of the nasal and paranasal sinuses characterized by symptoms of facial pain, nasal obstruction, and rhinorrhea. The treatment of CRS whether pre-or post-operative, often requires the delivery of medication to the maxillary sinus area and other areas of the sinus cavity. In addition to the delivery of medication, it is often desirable to have in place an intubation device for irrigation of the area.

There has been some attempt in the prior art to provide medication to remote, inaccessible areas. These include in bedding a product which progressively melts over a period of weeks or months. The problem which such devices is that there melting process is influenced by the contact with fluids and thus makes the delivery of medication unpredictable.

An additional problem is the desirability to keep a stent in place in a cavity, such as the sinus cavity, over the course of several weeks or months in order to continue to be able to treat a particular area. Prior art devices were very difficult at the very least to keep in place.

Accordingly, what is needed is a stent which solves all of the foregoing problems namely, which can deliver a precise amount of a specific medication and/or irrigation fluids to a generally remote or inaccessible area over a long period of time; which by its shape is designed to stay in place in the cavity and which can keep open any desired opening into a cavity.

SUMMARY

The present invention features a stent comprising a flexible tube having a proximal end, a distal end, and a passageway extending from the proximal end to the distal end. A first generally straight tube segment extends from the proximal end while a first generally curved segment extends from an end region of the first generally straight tube segment which is located away from the proximal end of the stent.

A second generally straight tube segment extends from an end region of the first curved segment away from the first generally straight tube segment. The second generally straight tube segment is arranged at an acute angle relative to the first generally straight tube segment. A second generally curved tube segment extending from one end of the second generally straight tube segment. The second generally curved tube segment includes a channel on an exterior surface which serves as a reservoir for storing medication(s) to be delivered into the cavity over an extended period of time.

The first generally curved tube segment includes at least one hole extending from the passageway to an exterior surface of the first generally curved tube segment. The second generally straight tube segment may also include at least one hole extending from the passageway to an exterior surface of the second generally straight tube segment. The hole in the second generally straight tube segment may have a larger diameter than the hole in the first generally curved tube segment.

The second generally curved tube segment is comprised of a plurality of straight and curved tube segments. The second generally curved tube segment may include a second generally curved tube portion, coupled to a third generally straight tube portion, coupled to a third generally curved tube portion, coupled to a fourth generally straight tube portion, coupled to a fourth generally curved tube portion, coupled to a fifth generally straight tube portion, coupled to a fifth generally curved tube portion.

BRIEF DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENTS

Figure 1:
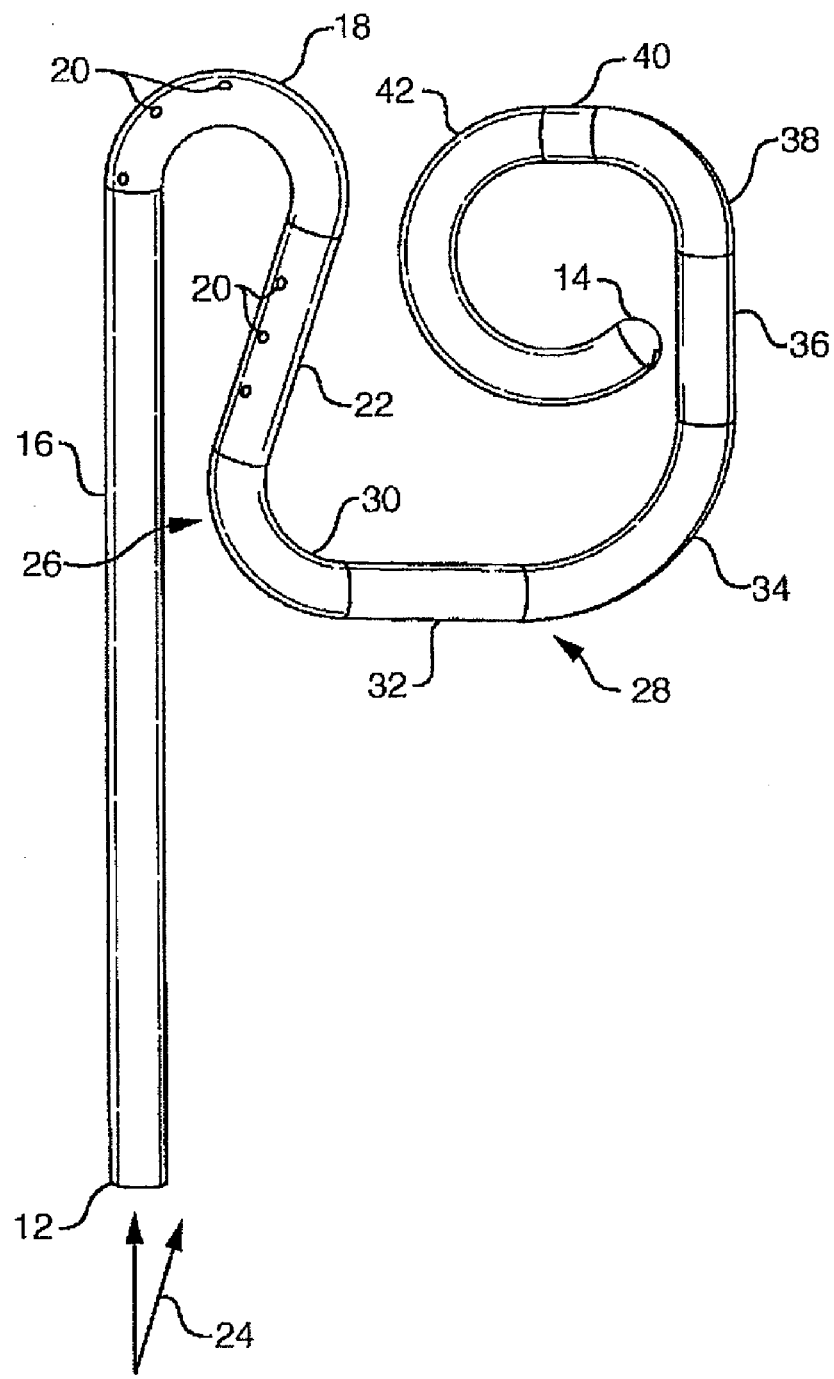
FIG. 1 is a systematic side view of the stent according to the present invention.

The present invention features a stent 10, FIG. 1, for a cavity having an opening in at least one side, such as a nasal cavity. Although the present invention will be explained with regard to a nasal cavity, this is not a limitation of the present invention as its use in any type of cavity, whether regular or irregular, that has an opening in at least one side is contemplated and can be achieved by someone skilled in the art. The stent according to the present invention features the ability to remain in place long-term, serves as a support for the opening of the cavity and is able to deliver an active medication using the irrigation features and the reservoir (storage) capabilities of the stent.

The stent 10 is comprised of a flexible hollow tube having a passageway in the center of the tube and having a proximal end 12 and a distal end 14. The stent is preferably made from a medical grade soft and resilient thermo-plastic material as is generally available for such products. A first generally straight tube segment 16 extends from the proximal end 12. A first generally curved tube segment 18 extends from one end of the first generally straight tube segment 16 proximate and the end of the tube away from the proximal end 12 of the stent.

In the preferred embodiment, the first generally curved tube segment 18 includes one or more holes 20 which extend from the interior passageway of the stent 10 to the exterior surface of the first generally curved tube segment 18. As will be explained in greater detail below, holes 20, if provided, serve to dispense medication and/or irrigation fluid which is introduced into the passageway of the tube into one of the sinus cavities (if the present invention is disposed in a sinus cavity) or any other cavity in which the stent according to the present invention is disclosed.

Coupled to the first generally curved tube segment 18 is a second generally straight tube segment 22. Tube segment 22 may also include, in the preferred embodiment, one or more holes 20 which also serve to dispense medication or irrigation fluid into the cavity into which the segment is placed. The holes 20 may be all the same size or may differ in size from tube segment to tube segment. In the present embodiment, the holes 20 are larger in the second straight segment 22 to favor irrigation in the cavity in which this portion is disposed. The length and the curvature of the first generally curved tube segment 18 is such that the second generally straight tube segment 22 is disposed at an acute angle 24 relative to the first generally straight tube segment 16. This orientation forms a narrowed passageway 26 between the first generally straight tube segment 16 and the second generally curved tube segment 28 which serves to hold or retain the stent in place when used in the sinus cavity as will be explained in greater detail in FIG. 4 below.

A second generally curved tube segment 28 is coupled to one end of the second generally straight tube section 22. The second generally curved tube segment 28 is comprised of a number of smaller generally straight and or generally curved tube portions as will be explained below.

In the preferred embodiment, for example, the second generally curved tube segment 28 may include a second generally curved tube portion 30, to which is coupled a third generally straight tube portion 32, coupled to a third generally curved tube portion 34 followed by a fourth generally straight tube portion 36, coupled to a fourth generally curved tube portion 38 coupled to a fifth generally straight tube portion 40 followed by a fifth generally curved tube portion 42. The above-mentioned combination of generally straight and generally curved tube portions is not a limitation of the present invention however as any combination of curved and/or straight tube segments is contemplated by the present invention.

Figure 2:
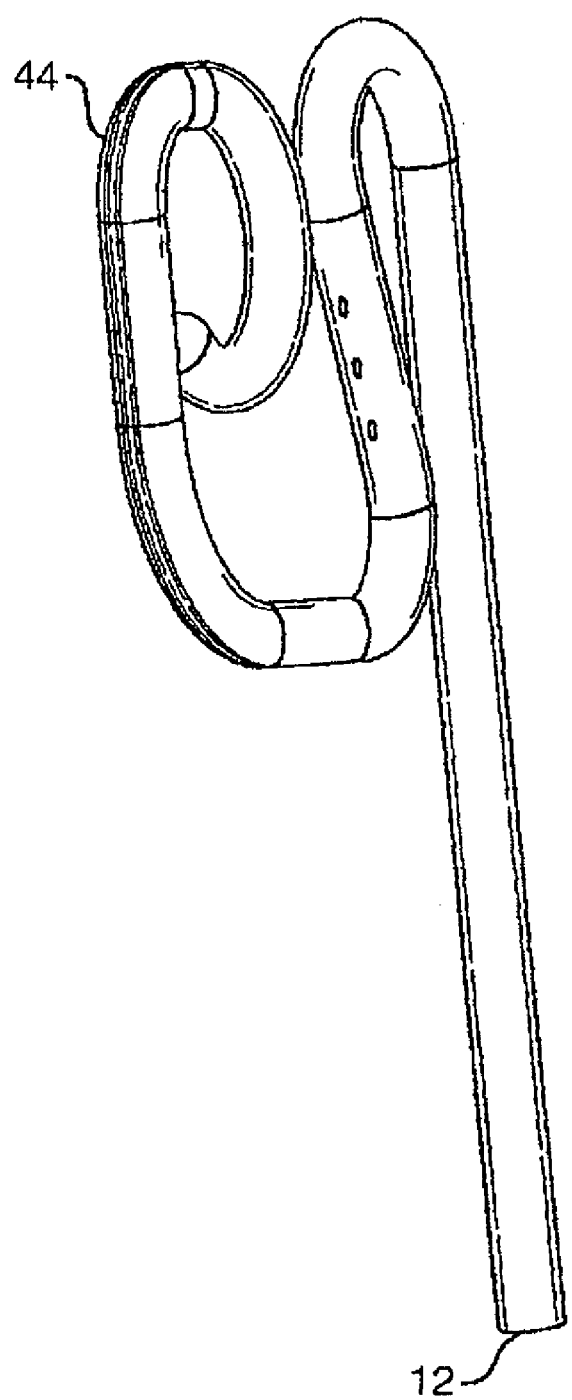
FIG. 2 is a schematic front view of the stent according to the present invention.

The second generally curved tube segment 28 includes, on an exterior surface, a channel 44, FIG. 2, which serves to carry and dispense medication which is introduced into the channel 44 prior to insertion of the stent into the patient.

Figure 3:
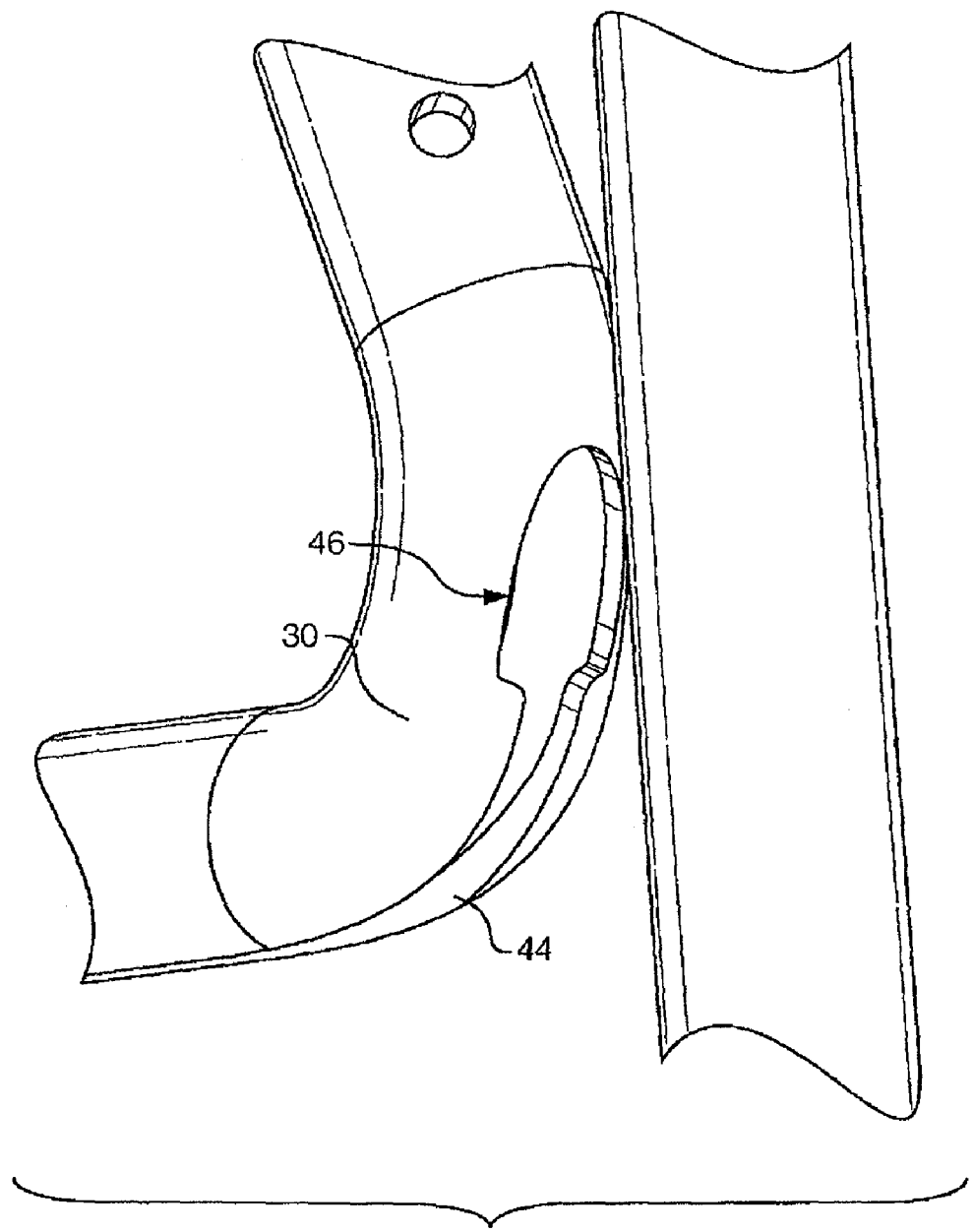
FIG. 3 is a partial close of view of the second generally curved segment of the stent according to the present invention.

It is contemplated that either the inserting physician or the stent manufacturer will place the proper medication in this channel prior to insertion of the stent into the patient or prior to the stent leaving the manufacturer. For example, it may be desired to have a steroid medication delivered to the patient over a period of time. An anti-fungal medication may also be desired. The medication(s) will be in a form such that delivery of the medication(s) occurs over a generally predetermined period of time. Such medications are well known in the art and include but are not limited to anti-fungal, antibiotics or antiseptic medication. Accordingly, the physician or pharmaceutical company will place in the channel 44 the proper amount and type(s) of desired medication(s). The channel 44 and channel starting region 46, FIG. 3, will be collectively sized to hold the proper amount of desired medication(s). The channel will be as long, wide and deep as required to hold the amount of medication to be dispensed. The channel 44 may be on the same side of the stent or may "spiral" around the exterior region of the stent.

The channel may be placed on any exterior surface of the stent. In the present embodiment, the channel 44 is on the side of the mucosa to be treated (the exterior part of the tube toward the side of the maxillary cavity). The groove or channel 44 has a volume formed by its with and depth which forms in essence a reservoir having a capacity which may be adjusted to different volumes of medication(s) needed for long term delivery of the desired medication(s).

The second generally curved tube segment 28 may include the channel starting region in the shape of a hole or larger depression 46 which extends inwardly from the exterior surface of the stent. In the present embodiment, the channel starting region 46 is located in the second generally curved tube portion 30.

Figure 4:
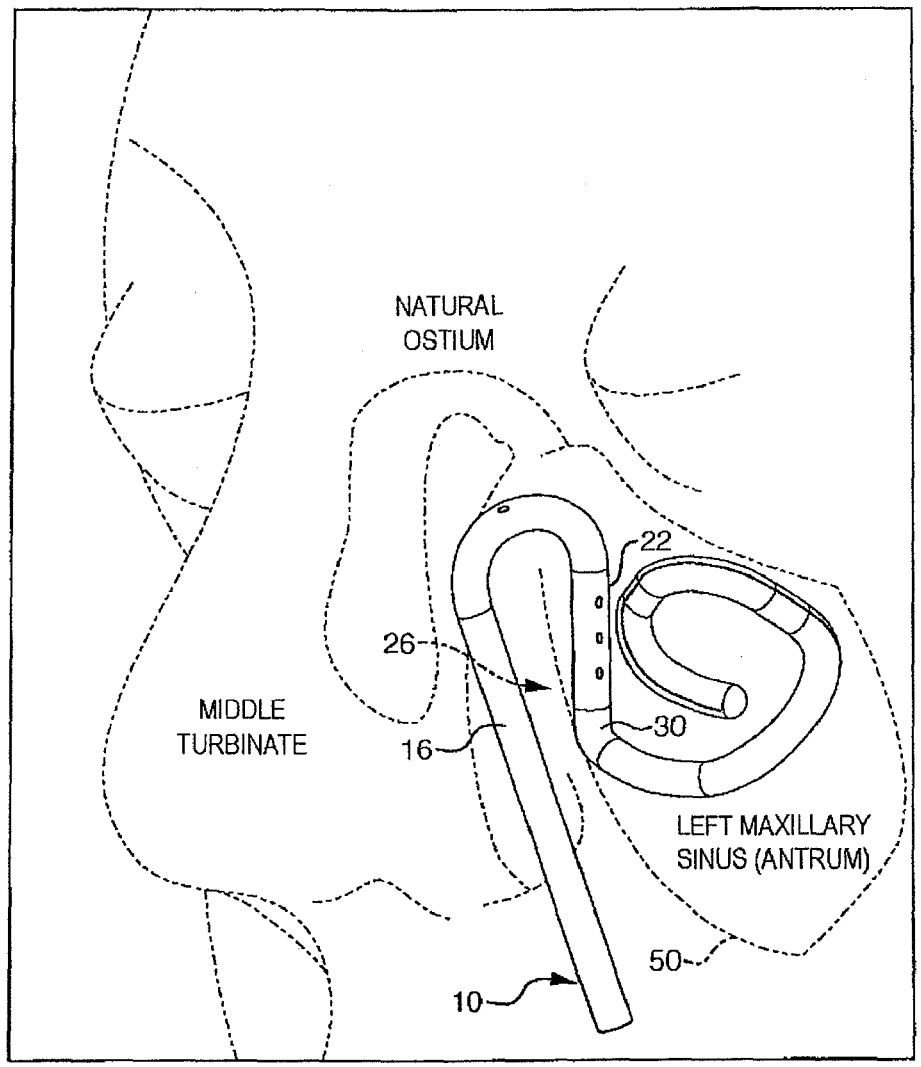
FIG. 4 is a schematic view of the stent of the present invention inserted in the sinus cavity.

The stent 10, FIG. 4 according to the present invention, may be inserted into any cavity but functions particularly well when inserted through the middle meatus of patients which have already been operated on. Insertion of the stent 10 is easily accomplished given its flexible and pliable nature by physicians performing endoscopic surgery as such insertion of other items are accomplished by them and as is well known to them.

One aspect of the present invention is the ability of the stent to remain in place. Fixation of the stent 10 is achieved by the "squeezing" effect between the first straight tube segment 16 and the second generally curved tube portion 30. The acute angle formed between the first generally straight tube segment 16 and the second generally straight tube segment 22 causes the stent 10 to curve back on itself and creates a narrow channel 26 and causes the second generally curved tube portion 32 push against the wall 50 of the sinus cavity. In addition, the segments 36, 38 and 40 (when applied in the sinus cavity) exert a pressure by segment 42 against segment 32 to add to the squeezing effect at the channel or region 26.

In this manner, the stent according to the present invention can remain in place for extended periods of time to allow the sinus or other cavity to be irrigated and to allow the stent to deliver the desired medication(s) over extended periods of time and to keep open the sinus cavity's ostium by keeping it away from the surrounding structures (i.e., middle turbinate for the maxillary sinus ostium).

Accordingly, the present invention provides a novel and nonobvious stent which remains in place in a cavity and which may be used to deliver various fluids to a remote area of the cavity using the hollow passageway formed by the stent tube.

Modifications and substitutions by one of ordinary skill in the art are considered to be within the scope of the present invention, which is not to be limited except by the allowed claims and their legal equivalents.

What we claim is:

1. A method for irrigating a maxillary sinus cavity comprising:

implanting at least a portion of a flexible tube in the maxillary sinus cavity, wherein the flexible tube comprises a proximal end, a distal end, a passageway extending therethrough, a first generally linear tube segment extending from the proximal end, a first generally curved tube segment extending from an end of the first generally linear tube segment, a second generally linear tube segment extending from an end of the first generally curved tube segment, a second generally curved tube segment extending from an end of the second generally linear tube segment, a third generally linear tube segment extending from an end of the second generally curved tube segment, and a third generally curved tube segment extending from an end of the third generally linear tube segment, wherein the second generally linear tube segment, the second generally curved tube segment, the third generally linear tube segment, and the third generally curved tube segment are positioned in the maxillary sinus cavity, and wherein at least a portion of the first curved tube segment is placed in a maxillary sinus ostium.

2. The method of claim 1 wherein the flexible tube comprises a thermo-plastic material.

3. The method of claim 1 wherein the flexible tube comprises one or more holes extending from the passageway to an exterior surface of the flexible tube.

4. The method of claim wherein the first generally curved tube segment comprises one or more holes extending from the passageway to an exterior surface of the flexible tube.

5. The method of claim 1 wherein the second generally linear tube segment comprises one or more holes extending from the passageway to an exterior surface of the flexible tube.

6. The method of claim 1 wherein the flexible tube comprises a channel on an exterior surface of the flexible tube.

7. The method of claim 6 wherein the channel comprises one or more medications.

\* \* \* \* \*